(12) United States Patent
Rodriguez Alvarez et al.

(10) Patent No.: US 12,297,246 B2
(45) Date of Patent: May 13, 2025

(54) INTERLEUKIN-15 ACTIVITY ANTAGONIST PEPTIDE

(71) Applicant: CENTRO DE INGENIERÍA GENÉTICA Y BIOTECNOLOGÍA, Havana (CU)

(72) Inventors: Yunier Rodriguez Alvarez, Artemisa (CU); Hilda Elisa Garay Perez, Havana (CU); Osvaldo Reyes Acosta, Havana (CU); Ania Cabrales Rico, Havana (CU)

(73) Assignee: CENTRO DE INGENIERÍA GENÉTICA Y BIOTECNOLOGÍA, Havana (CU)

( * ) Notice: Subject to any disclaimer, the term of this patent is extended or adjusted under 35 U.S.C. 154(b) by 194 days.

(21) Appl. No.: 16/958,472

(22) PCT Filed: Dec. 21, 2018

(86) PCT No.: PCT/CU2018/050006
§ 371 (c)(1),
(2) Date: Jun. 26, 2020

(87) PCT Pub. No.: WO2019/129314
PCT Pub. Date: Jul. 4, 2019

(65) Prior Publication Data
US 2024/0228568 A1    Jul. 11, 2024

(30) Foreign Application Priority Data
Dec. 29, 2017    (CU) .................................. 2017-0177

(51) Int. Cl.
*C07K 14/54* (2006.01)
*A61P 19/02* (2006.01)
*A61P 37/06* (2006.01)
*A61K 38/00* (2006.01)

(52) U.S. Cl.
CPC .......... *C07K 14/5443* (2013.01); *A61P 19/02* (2018.01); *A61P 37/06* (2018.01); *A61K 38/00* (2013.01)

(58) Field of Classification Search
CPC ................................................. C07K 14/5443
See application file for complete search history.

(56) References Cited

U.S. PATENT DOCUMENTS

2016/0306918 A1    10/2016    Azimi et al.

FOREIGN PATENT DOCUMENTS

| EP | 1801119 A1 | 6/2007 |
| EP | 2354152 A1 | 8/2011 |
| WO | 2019129314 A1 | 7/2019 |

OTHER PUBLICATIONS

Grabstein et al (May 13, 1994), Science, vol. 264, pp. 965-968.*
Savio, Alicia Santos, et al., "Enhancement of the Inhibitory Effect of an IL-15 Antagonist Peptide by Alanine Scanning," Journal of Peptide Science 18, No. 1, pp. 25-29 (2012).
Santos, Alicia, et al., "Identification of an Interleukin-15 Antagonist Peptide that Binds to IL-15Rα," Biotecnologia Aplicada 25, No. 4, pp. 320-324 (2008).
International Search Report on International Application No. PCT/CU2018/050006, dated Apr. 30, 2019.

* cited by examiner

*Primary Examiner* — Prema M Mertz
(74) *Attorney, Agent, or Firm* — Hoffmann & Baron LLP

(57) ABSTRACT

The present invention discloses an antagonist peptide of the Interleukin-15 (IL-15) activity, which is characterized in that it comprises an amino acid sequence identified as SEQ ID No. 5 or SEQ ID No. 12, or a homodimer of these peptides, as well as a nucleic acid that encodes for the peptide with the sequence identified as SEQ ID No. 5 or SEQ ID No. 12. Pharmaceutical compositions comprising said peptides or nucleic acids encoding said sequences are part of the invention. In addition, it provides the use of an IL-15 antagonist peptide comprising the amino acid sequence identified as SEQ ID No. 5 or SEQ ID No. 12, or a homodimer of these peptides, for the manufacture of a medicament. The invention contemplates a method for the treatment of a disease related to the IL-15 overexpression, prostate and kidney cancer.

Figure 1:
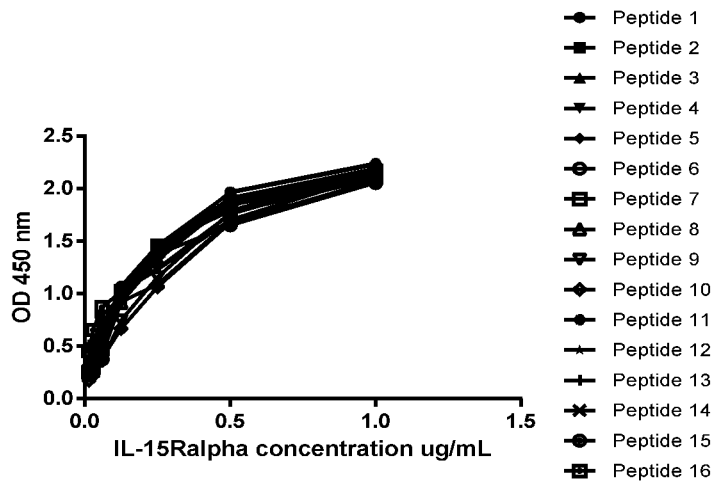

2 Claims, 2 Drawing Sheets
Specification includes a Sequence Listing.

A

B

A

B

C

D

INTERLEUKIN-15 ACTIVITY ANTAGONIST PEPTIDE

This application is a U.S. National Phase of, and Applicant claims priority from, International Patent Application No. PCT/CU2018/050006, filed Dec. 21, 2018, which claims priority from CU 2017/0177, filed Dec. 29, 2017, each of which is incorporated herein by reference in its entirety.

SEQUENCE LISTING

A Sequence Listing conforming to the rules of WIPO Standard ST.25 is hereby incorporated by reference. Said Sequence Listing has been filed as an electronic document via the USPTO patent electronic filing system in ASCII formatted text. The electronic document, created on Dec. 13, 2024, is entitled "976-107_PCT_US_ST25_2024-12-13.txt", and is 4,300 bytes in size.

FIELD OF TECHNIQUE

The present invention relates to the branch of molecular pharmacology and human medicine, in particular, with the obtention of antagonist peptides of the Interleukin-15 (IL-15) activity, derivatives of said cytokine, which have a greater effect than an antagonist peptide previously identified. Due to its biological activity, the antagonist peptides of the invention are useful for the treatment of diseases related to non-regulated expression of IL-15 and/or alpha subunit of the IL-15 receptor (IL-15Rα).

STATE OF THE PRIOR ART

IL-15 was initially identified as a T cell activating factor (Grabstein, K. H. et al., Science 1994, 264, 965-968; Burton, J. D. et al., Proc. Natl. Acad. Sci. USA 1994, 91, 4935-4939). Despite the broad distribution of messenger ribonucleic acid (mRNA) of IL-15, the expression of the protein is strongly regulated at the post-transcriptional level (Bamford R N. et al., J. Immunol 1998, 160: 4418-4426; Kurys G, et al., J Biol Chem 2000, 275: 30653-30659). This cytokine can be expressed as integral membrane protein (Musso et al., Blood 1999, 93: 3531-3539) or in soluble form, acting as a receptor or ligand, respectively. IL-15 expressed as an integral membrane protein interacts with soluble IL-15Rα and triggers an inverse signaling mechanism that involves the secretion of pro-inflammatory cytokines (Tumor Necrosis Factor α (TNF-α), Interleukin-6 (IL-6), Interleukin-8 (IL-8)) and cell migration (Budagian V. et al., J. Biol Chem 2004, 40: 42192-42201). The IL-15 biological effects as ligand are mediated through binding to a trimeric receptor on the cell membrane composed by α, β, and $\gamma_c$ subunits. These subunits can be co-expressed in the same cell, or it can happen that the IL-15 bound to a subunit is presented to neighboring cells that express only β and $\gamma_c$ subunits, a mechanism known as trans presentation (Burkett P. R. et al. J Exp. Med 2004, 200: 825-834). While β and $\gamma_c$ subunits are shared with other cytokines, the IL-15Rα is specific for IL-15 (Giri J G et al. EMBO J 1995, 14: 3654-63).

The unregulated expression of IL-15 has been associated with the pathogenesis and development of autoimmune and inflammatory diseases, such as Crohn's disease (Kirman I., Am. J. Gastroenterol. 1996, 91: 1789-1794), psoriasis (Rückert R J Immunol 2000, 165: 2240-2250), some types of leukemias (Yamada Y. Leukemia and Lymphoma 1999, 35: 37-45) and rheumatoid arthritis (RA) (McInnes I B, Immunology Today 1998, 19: 75-79).

The experimental evidences shown in the works of McInnes and Ziolkowska ratify to IL-15 as an attractive therapeutic target, particularly in RA. These findings are: high IL-15 concentrations in synovial fluid, increased expression in membrane of synovial cells, stimulation of TNF-α, IL-6 and IL-17 secretion, and migration of T cells into the synovial fluid of RA patients (McInnes I. B. et al., Nat Med 1997, 3: 189-195; Ziolkowska M. et al., J Immunology 2000, 164: 2832-2838). In an animal model of the disease, Yoshihara et al. demonstrated that IL-15 exacerbates collagen-induced arthritis in a transgenic mouse for this cytokine (Yoshihara K. et al., Eur J. Immunol. 2007, 37: 2744-2752). All these elements suggest that IL-15 antagonists could be useful in the treatment of RA and other autoimmune and inflammatory diseases related to the overexpression of this cytokine.

In this sense, have been developed IL-15 muteins (mutated proteins) that have substitutions in the $Asp^{56}$ and $Gln^{156}$ and antibodies against receptor subunits, which act as antagonist molecules (patents No. U.S. Pat. Nos. 6,177,079, 6,168,783, 6,013,480, 6,001,973, 9,706,931, and International Patent Application No. WO9741232). Other muteins described by Bernard et al may act as agonists or antagonists of the IL-15 (Bernard J. et al., J Biol Chem 2004, 279: 24313-24322). However, these entities have not resulted in a commercially available drug for the therapy of diseases associated with IL-15 overexpression.

In 2006, an IL-15 antagonist peptide that blocks the interaction of this cytokine with IL-15Rα was identified (International Patent Application No. WO2006/029578). The half maximal inhibitory concentration ($IC_{50}$) calculated for this peptide is 130 μM. Studies of optimization of said antagonist, reflected in the Patent Application in Cuba No. 2008-0184, allowed the identification of a more active peptide ($IC_{50}$ 24 μM), but less soluble than the starting peptide compound. This low solubility hindered its development as a drug.

Taking into account the high affinity of IL-15 for IL-15Rα, it is necessary to identify molecular entities with a higher inhibitory activity than the antagonists already described; what would allow the obtention of more effective drugs for the treatment of RA and other autoimmune and inflammatory diseases related to the IL-15 overexpression.

DETAILED DESCRIPTION OF THE INVENTION

This invention contributes to solve the aforementioned problem by providing IL-15 activity antagonist peptides; which are characterized in that they comprise an amino acid sequence identified as SEQ ID No. 5 or SEQ ID No. 12 or a homodimer of these peptides. These peptides were obtained from amino acid substitutions with D conformation in the peptide consisting of SEQ ID NO: 1.

These antagonist peptides are more active than the one described in patent application No. WO2006/029578, since they have a lower $IC_{50}$ than the starting antagonist. The optimization was achieved by replacing one or two amino acid with L conformation by their corresponding residues with D conformation, in the original antagonist. Other antagonists identified in the invention are the result of the formation of a homodimer among the most active monomers, chemically linked through the free cysteines present in them. For the purposes of the present invention, an antagonist of the IL-15 activity is that entity which blocks the interaction of the cytokine with its receptor, thereby inhibiting the biological effects of the cytokine.

In the context of the invention, a homodimer of the peptides with the amino acid sequence identified as SEQ ID No. 5 or SEQ ID No. 12 is that peptide where two identical monomers of said peptides are chemically linked. Since it is known that the introduction of D amino acids (D-aa) into the peptide sequence increases its stability, it was surprising that in the invention some substitutions of this type abrogated the capacity as antagonist of IL-15 activity which possessed the original peptide, denominated in the invention as peptide 1. In the invention, 10 peptides with a change of L amino acids (L-aa) by D-aa were generated; which were evaluated in a biological activity assay using the IL-15-dependent cell line, CTLL-2. The homodimer of the peptide identified with SEQ ID No. 5 was also obtained. Additionally, two peptides with two D-aa were designed (Peptide 13 and peptide 15), and by chemical synthesis the corresponding dimer was obtained (Peptide 14 and peptide 16).

In general, the application of a small peptide, as IL-15 antagonist, has the advantage of selectively blocking the binding of IL-15 to IL-15Rα; inhibiting the effects of the cytokine due to the interaction with said receptor subunit.

The binding capacity of peptides to IL-15Rα was evaluated by an ELISA-type immunoassay, and its effect on the inhibition of the IL-15 biological activity was determined in the CTLL-2 cell proliferation assay (Rodriguez-Alvarez et al., Biotecn Aplic 2014; 31: 291-6). Additionally, the effect of these peptides on the secretion of two inflammatory cytokines (TNF-α and IL-6) was determined by ex vivo assays with cells isolated from the synovial fluid of patients with RA.

In these experiments it was shown that only four variants, named Peptide 5, peptide 12, peptide 13 and peptide 14, are more active than Peptide 1 in inhibiting the proliferation of CTLL-2 cells induced by IL-15 and the secretion of IL-6 and TNF-α. These peptides are completely soluble, which represents an advantage over the peptide of Cuban patent application No. 2008-0184. Peptide 12 showed the greatest effect, with an $IC_{50}$ of 8 µM. This peptide was also more active than the original antagonist (Peptide 1) in the inhibition of TNF-α and IL-6 secretion induced by IL-15Rα in synovial cells from RA patients.

These antagonist peptides (Peptide 5, peptide 12, peptide 13 and peptide 14) can inhibit the effect of reverse signaling through membrane IL-15, referred by Budagian et al in 2004; since they bind to the IL-15Rα as described in the present invention. Thus, they are useful in inhibiting the binding of soluble IL-15Rα to IL-15 expressed on the membrane of the tumor cell. In an embodiment of the invention the peptide is obtained by genetic manipulation or chemical synthesis.

In another aspect, the invention discloses a nucleic acid that codes for a peptide comprising the amino acid sequence identified as SEQ ID No. 5 or SEQ ID No. 12, since its expression product is capable of binding to IL-15Rα or its soluble fraction, and inhibits the biological activity of the cytokine. A vector containing said nucleic acid sequences can be used as an alternative for the expression of antagonist peptides of the invention.

Another aspect of the invention is a pharmaceutical composition comprising an IL-15 antagonist peptide with an amino acid sequence identified as SEQ ID No. 5 or SEQ ID No. 12, or a homodimer of one of these peptides, and pharmaceutically acceptable excipients. In the invention, the composition could be of topical application for the treatment of diseases that manifest in the skin, and in whose lesions the IL-15 overexpression is detected, such as psoriasis and cutaneous T-cell lymphoma.

In an embodiment of the invention, the pharmaceutical composition is characterized in that it comprises the nucleic acid that codes for a peptide comprising the amino acid sequence identified as SEQ ID No. 5 or SEQ ID No. 12 and pharmaceutically acceptable excipients.

Another aspect of the invention is the use of a peptide that comprises the amino acid sequence identified as SEQ ID No. 5 or SEQ ID No. 12, or a homodimer of these peptides, for the manufacture of a medicament. In one embodiment of the invention, the medicament is used for the treatment of diseases related to IL-15 overexpression. In a particular embodiment, the disease related to IL-15 overexpression is an autoimmune disease selected from the group consisting of RA, Crohn's disease, ulcerative colitis and psoriasis. In another embodiment, the medicament is used for the treatment of prostate or kidney cancer.

The invention also contemplates a method for the treatment of a disease related with IL-15 overexpression that comprises the administration to an individual that needs it of a therapeutically effective amount of the pharmaceutical composition that comprises a peptide with the sequence of amino acids identified as SEQ ID No. 5 or SEQ ID No. 12, or a homodimer of these peptides. In another aspect, the method can involve the administration of the pharmaceutical composition that comprises the nucleic acid encoding the sequence peptide SEQ ID No. 5 or SEQ ID No. 12. In a particular embodiment, the disease related with the IL-15 overexpression that is treated with the method of the invention is an autoimmune disease selected from the group consisting of RA, Crohn's disease, ulcerative colitis and psoriasis.

In the RA treatment method of the present invention, the selected antagonist peptides are administered alone or in combination with some other drug, such as steroidal anti-inflammatory drugs (such as corticosteroids) and disease modifying drugs (for example methotrexate).

In another aspect, the invention discloses a method for the treatment of prostate or kidney cancer that comprises the administration to an individual that needs it of a therapeutically effective amount of the pharmaceutical composition that comprises a peptide with the sequence of amino acids identified as SEQ ID No. 5 or SEQ ID No. 12, a homodimer of these peptides or nucleic acids that codes for the peptide of sequence SEQ ID No. 5 or SEQ ID No. 12.

BRIEF DRAWINGS DESCRIPTION

FIG. 1. Binding of the identified peptides to the IL-15Rα, detected by an ELISA-type system.

Figure 2:
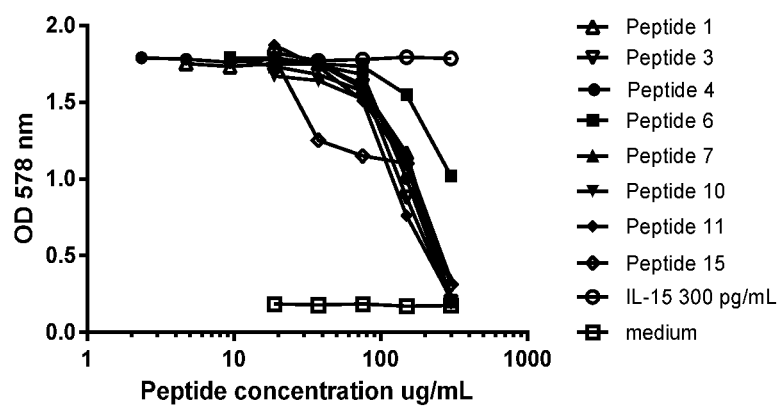
Figure 2:
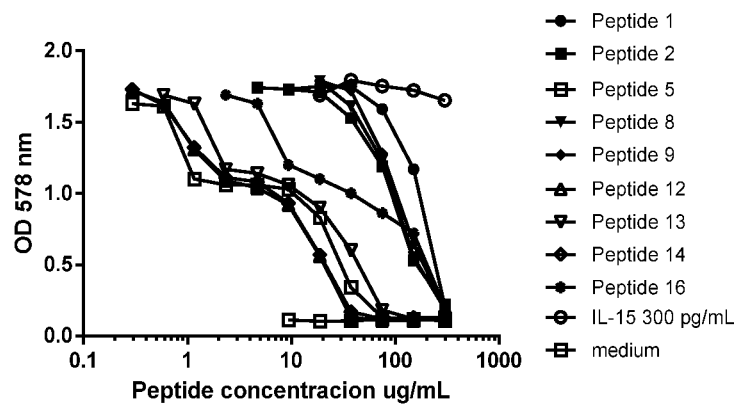

FIG. 2. Effect of the identified peptides on the IL-15-induced proliferation in CTLL-2 cell line. A. Evaluation of peptides 3, 4, 6, 7, 10, 11 and 15. B. Evaluation of peptides 2, 5, 8, 9, 12, 13, 14 and 16. In all assays, the peptide 1 was evaluated.

Figure 3:
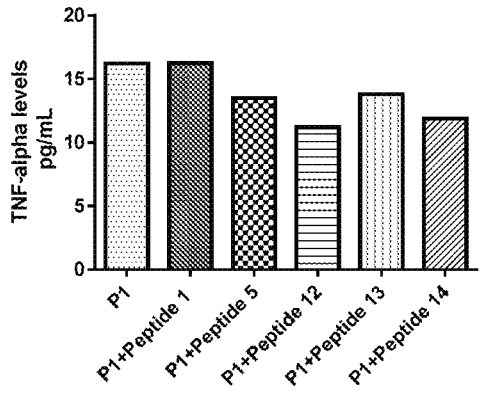
Figure 3:
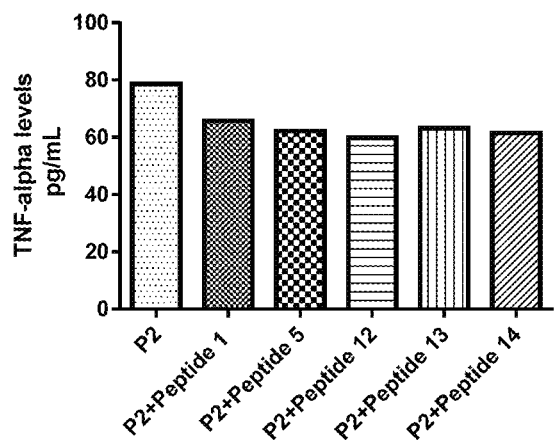
Figure 3:
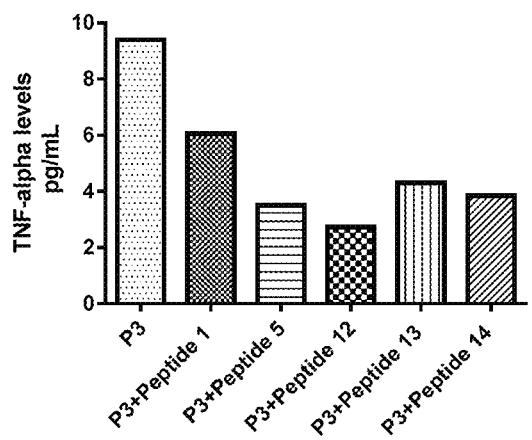
Figure 3:
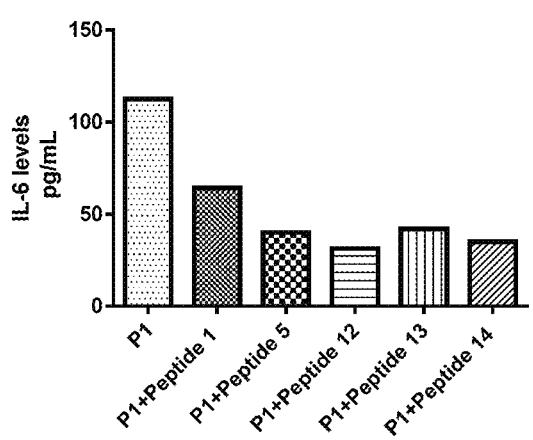

FIG. 3. TNF-α and IL-6 levels detected in the supernatant of synovial cells from patients treated with selected peptides for this assay. For TNF-α, samples of three patients were evaluated (P1-P3, Panels A-C). For IL-6, the sample of one patient was evaluated (Panel D).

DETAILED DISCLOSURE OF EMBODIMENTS/EXAMPLES OF REALIZATION

Example 1. Synthesis of Peptides Comprising D-Aa

Design

From the peptide identified in the sequence list of this invention as SEQ ID No. 1 (also referred to as Peptide 1), a panel of peptides was designed in which the punctual substitution of each amino acid residue with L-conformation was performed by the same residue with D-conformation. In this invention, from peptide 2 to peptide 11 correspond to the amino acid sequences identified with the same number (SEQ ID No. 2-SEQ ID No. 11). Also, the chemical homodimer of the peptide with SEQ ID NO. 5 was designed, which was named Peptide 12.

Additionally, peptides with two D-aa were designed to combine the amino acid residues that would result in the greatest antagonistic effect with respect to Peptide 1. In this way, Peptide 13 (whose sequence corresponds to SEQ ID No. 12) and Peptide 15 (whose sequence corresponds to SEQ ID No. 13) were designed. Also, were designed the Peptide 14, as a homodimer of the peptide of SEQ ID NO. 12 and Peptide 16, as a homodimer of the peptide of SEQ ID NO. 13.

Peptide Synthesis

The monomeric peptides were synthesized by the Fmoc/tBu strategy in syringes. The Fmoc-AM-MBHA resin was used at 0.54 mmol/g, and the synthesis protocol with mechanical agitation was followed (Field G B and Noble R L Int. J. Peptide Protein Res. 1990; 35 (3): 161-214). In desired variants, the dimerization of the peptide was carried out by oxidation of the cysteine with 20% dimethyl sulfoxide (Andreu D. et al., Peptide Synthesis Protocols, Humana Press Inc.: Totowa, New Jersey, 1994; 91-116). All peptides were purified by Reverse Phase chromatography (RP-HPLC), and their sequence was verified by mass spectrometry (ESI-MS). All peptides were obtained with more than 95% of purity, and there was correspondence between the mass obtained and that expected according to the corresponding amino acid sequence, as shown in Table 1.

TABLE 1

Characterization of the obtained peptide variants.

| | | Identity by ESI-MS | |
| --- | --- | --- | --- |
| Peptide | Purity (%) | Theoretical monoisotopic MM (Da) | Experimental MM (Da) |
| 1 | 98.69 | 1152.53 | 1151.65 |
| 2 | 99.18 | 1152.53 | 1151.65 |
| 3 | 97.88 | 1152.53 | 1151.65 |
| 4 | 99.31 | 1152.53 | 1151.65 |
| 5 | 99.72 | 1152.53 | 1151.65 |
| 6 | 97.92 | 1152.53 | 1151.65 |
| 7 | 99.41 | 1152.53 | 1151.65 |
| 8 | 99.08 | 1152.53 | 1151.65 |
| 9 | 96.76 | 1152.53 | 1151.65 |
| 10 | 98.88 | 1152.53 | 1151.65 |
| 11 | 98.60 | 1152.53 | 1151.65 |
| 12 | 97.46 | 2303.05 | 2301.29 |
| 13 | 99.40 | 1152.53 | 1151.65 |
| 14 | 99.57 | 2303.05 | 2301.29 |
| 15 | 99.08 | 1152.53 | 1151.65 |
| 16 | 99.71 | 2303.05 | 2301.29 |

Example 2. Evaluation of the Binding Capacity of the Peptides to IL-15Rα

Once the synthetic peptides were obtained and characterized, their binding capacity to IL-15Rα was determined. This evaluation was carried out by means of an ELISA type test. In addition, the % inhibition of the formation of the IL-15/IL-15Rα complex presented by each peptide was calculated. Both the procedure for the ELISA-type test and the equation used to calculate the % inhibition of the formation of the IL-15/IL-15Rα complex are detailed in the article published by Santos et al in 2012 (Santos A. et al. J. Pept. Sci. 2012; 18: 25-29).

As seen in FIG. 1, all evaluated peptides recognized IL-15Rα immobilized on the ELISA plate. Neither the replacement of L-aa with D-aa in the original antagonist peptide, nor the chemical dimerization of some of the new designed peptides, affected the binding capacity of these peptides to IL-15Rα.

The highest % inhibition of IL-15/IL-15Rα complex formation was obtained for Peptide 5, Peptide 12, Peptide 13 and Peptide 14, with 92, 96, 89 and 92%, respectively. These inhibition percentages are greater than the one reported by Santos et al in 2012 for Peptide 1, which showed a 70%.

Example 3. Effect of the Peptides on the CTLL-2 Cell Line Proliferation

The proliferation of the CTLL-2 cell line is dependent on IL-15. Molecular entities that bind to IL-15 or its receptor subunit inhibit the proliferation of this cell line. To evaluate the antagonist capacity of peptides designed and obtained in the present invention, was followed the procedure described by Santos et al in 2012. The effect of the identified peptides on the IL-15-induced proliferation in CTLL-2 cells was summarized in FIGS. 2A and 2B. Peptide 1 was included in all assays. FIG. 2A shows the results of those synthetic peptides that showed a similar effect to Peptide 1 in this biological activity assay. On the other hand, FIG. 2B shows the proliferation of said cell line in the presence of peptides that had a greater IL-15 antagonist effect than Peptide 1.

The realization of this colorimetric assay allowed calculating the $IC_{50}$ value of each peptide, for a fixed IL-15 concentration of 300 µg/mL. The $IC_{50}$ values for each peptide are shown in Table 2. Product of the substitutions of a residue with L-conformation by D-conformation we found peptides, such as Peptide 3, Peptide 4, Peptide 6, Peptide 7, Peptide 10, Peptide 11 and Peptide 15, which show equal or less antagonist effect than the original peptide; such as shown in Table 2. These peptides had an $IC_{50}$ equal or greater than showed by Peptide 1. Also, Peptide 2, Peptide 5, Peptide 8, Peptide 9, Peptide 12, Peptide 13, Peptide 14 and Peptide 16 showed a greater antagonist effect (lower ICs) than Peptide 1.

TABLE 2

$IC_{50}$ values of the evaluated peptides in the CTLL-2 cell proliferation assay.

| Peptide | $IC_{50}$ (µM) |
| --- | --- |
| 1 | 130 |
| 2 | 100 |
| 3 | 142 |
| 4 | 159 |
| 5 | 28 |
| 6 | 292 |

TABLE 2-continued

IC$_{50}$ values of the evaluated peptides
in the CTLL-2 cell proliferation assay.

| Peptide | IC$_{50}$ (μM) |
|---------|----------------|
| 7       | 168            |
| 8       | 103            |
| 9       | 118            |
| 10      | 134            |
| 11      | 133            |
| 12      | 8              |
| 13      | 29             |
| 14      | 12             |
| 15      | 296            |
| 16      | 56             |

In this assay, the greatest antagonist effect on IL-15-induced proliferation was shown by Peptide 12, chemical homodimer of the peptide of SEQ ID NO. 5, which has the punctual substitution of L-Ala by D-Ala. In this peptide, the Cys residue is involved in the formation of the disulfide bond between the two monomers. This peptide is three times more active than its monomeric form (Peptide 5), and 16 times more active than the original peptide (Peptide 1). Peptide 13, which contains two D-aa in its sequence, was as active as Peptide 5 and more active than Peptide 1. However, the other variant with two D-aa (Peptide 15) is less active than Peptide 1.

In correspondence with the results obtained in the CTLL-2 cells, the peptides with the highest antagonist effect (Peptide 5, Peptide 12, Peptide 13 and Peptide 14) showed greater percentages of inhibition of the IL-15/IL-15Rα complex formation than Peptide 1.

As a whole, the results obtained indicate that it is not obvious that the substitution of L-aa for D-aa, from Peptide 1, results in a greater antagonist effect of IL-15 activity, although it is known that the introduction of D-aa in a peptide improves its stability. Of all the possible residues, only the substitution of alanine guarantees this effect. Nor can it be anticipated that the double change of L-aa by D-aa will improve the capacity as antagonist, since Peptide 13 and Peptide 15, which contain two D-aa in their sequence, showed an opposite effect.

Example 4. Evaluation of the Effect of Selected Peptides on the Secretion of TNF-α and IL-6 in Synovial Cells from RA Patients It is known that IL-15 constitutes an attractive target for the treatment of RA. This cytokine induces the expression of others classified as inflammatory, such as TNF-α and IL-6. Against these two proteins numerous drugs have been developed which are currently biological therapies, approved by the Food and Drug Administration of the United States, for the treatment of RA.

Taking into account these antecedents, it is important to evaluate the effect of IL-15 antagonists on the secretion of TNF-α and IL-6 by ex vivo tests with synovial cells of RA patients. To determine the effect of selected peptides on the secretion of TNF-α, a procedure previously described was performed (Santos A. et al., J. Pept. Sci. 2012; 18: 25-29). TNF-α levels were determined by a commercially available ELISA-type immunoassay (R&D, USA). This measurement was made in the culture supernatant of synovial cells from three patients with RA (P1, P2, P3).

The effect of the same peptides on the secretion of IL-6, mediated by the binding of soluble IL-15Rα to the IL-15 present in the membrane of the synovial cells from RA patient (P1), was also evaluated; following the procedure described in a previous report (Machado A C αal., Arthritis, 2012, Article ID 943156). The assay was performed in 96-well plates, incubating 2×10$^5$ cells/well, stimulated or not with IL-15Rα (100 ng/mL) and treated with 100 μg/mL of the selected peptides (Peptides 1, 5, 12, 13 and 14). After 48 h of incubation, the culture supernatant was collected and IL-6 levels were determined through a commercial ELISA system (R&D, USA).

A shown in FIG. 3, Peptides 5, 12, 13 and 14, selected for this assay, were more active than the original antagonist (Peptide 1) in the inhibition of TNF-α secretion (FIGS. 3A, 3B, and 3C) and IL-6 secretion (FIG. 3D).

INCORPORATION OF SEQUENCE LISTING

Incorporated herein by reference in its entirety is the Sequence Listing for the application. The Sequence Listing is disclosed on a computer-readable ASCII text file titled, "Sequence_Listing_976-107PCTUS.txt", created on Nov. 5, 2021. The sequence_listing.txt file is 3.10 KB in size.

The invention claimed is:

1. An isolated peptide which antagonizes the activity of Interleukin-15 (IL-15), which peptide consists of:
   (i) the amino acid sequence as set forth in SEQ ID NO: 5, wherein the Ala residue is a D-amino acid residue, or monomers thereof to form a homodimer linked through cysteine residues; or
   (ii) the amino acid sequence set forth in SEQ ID NO: 12, wherein the first Lys residue and the Ala residue are D-amino acid residues, or monomers thereof to form a homodimer linked through cysteine residues.

2. A pharmaceutical composition comprising the peptide of claim 1 and pharmaceutically acceptable excipients.

SEQUENCE LISTING

```
<160> NUMBER OF SEQ ID NOS: 13

<210> SEQ ID NO 1
<211> LENGTH: 10
<212> TYPE: PRT
<213> ORGANISM: Homo sapiens

<400> SEQUENCE: 1

Lys Val Thr Ala Met Lys Cys Phe Leu Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of the Sequence: Peptide 2
<220> FEATURE:
<221> NAME/KEY: MOD_RES
<222> LOCATION: 1
```

```
<223> OTHER INFORMATION: D-Lysine

<400> SEQUENCE: 2

Lys Val Thr Ala Met Lys Cys Phe Leu Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of the Sequence: Peptide 3
<220> FEATURE:
<221> NAME/KEY: MOD_RES
<222> LOCATION: 2
<223> OTHER INFORMATION: D-Valine

<400> SEQUENCE: 3

Lys Val Thr Ala Met Lys Cys Phe Leu Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of the Sequence: Peptide 4
<220> FEATURE:
<221> NAME/KEY: MOD_RES
<222> LOCATION: 3
<223> OTHER INFORMATION: D-Threonine

<400> SEQUENCE: 4

Lys Val Thr Ala Met Lys Cys Phe Leu Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of the Sequence: Peptide 5
<220> FEATURE:
<221> NAME/KEY: MOD_RES
<222> LOCATION: 4
<223> OTHER INFORMATION: D-Alanine

<400> SEQUENCE: 5

Lys Val Thr Ala Met Lys Cys Phe Leu Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of the Sequence: Peptide 6
<220> FEATURE:
<221> NAME/KEY: MOD_RES
<222> LOCATION: 5
<223> OTHER INFORMATION: D-Methionine

<400> SEQUENCE: 6

Lys Val Thr Ala Met Lys Cys Phe Leu Leu
1               5                   10

<210> SEQ ID NO 7
<211> LENGTH: 10
<212> TYPE: PRT
```

```
<213> ORGANISM: Artificial Sequence
<220> FEATURE:
<223> OTHER INFORMATION: Description of the Sequence: Peptide 7
<220> FEATURE:
<221> NAME/KEY: MOD_RES
<222> LOCATION: 6
<223> OTHER INFORMATION: D-Lysine

<400> SEQUENCE: 7

Lys Val Thr Ala Met Lys Cys Phe Leu Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of the Sequence: Peptide 8
<220> FEATURE:
<221> NAME/KEY: MOD_RES
<222> LOCATION: 7
<223> OTHER INFORMATION: D-Cysteine

<400> SEQUENCE: 8

Lys Val Thr Ala Met Lys Cys Phe Leu Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of the Sequence: Peptide 9
<220> FEATURE:
<221> NAME/KEY: MOD_RES
<222> LOCATION: 8
<223> OTHER INFORMATION: D-Phenylalanine

<400> SEQUENCE: 9

Lys Val Thr Ala Met Lys Cys Phe Leu Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of the Sequence: Peptide 10
<220> FEATURE:
<221> NAME/KEY: MOD_RES
<222> LOCATION: 9
<223> OTHER INFORMATION: D-Leucine

<400> SEQUENCE: 10

Lys Val Thr Ala Met Lys Cys Phe Leu Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of the Sequence: Peptide 11
<220> FEATURE:
<221> NAME/KEY: MOD_RES
<222> LOCATION: 10
<223> OTHER INFORMATION: D-Leucine

<400> SEQUENCE: 11

Lys Val Thr Ala Met Lys Cys Phe Leu Leu
```

```
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of the Sequence: Peptide 13
<220> FEATURE:
<221> NAME/KEY: MOD_RES
<222> LOCATION: 1
<223> OTHER INFORMATION: D-Lysine
<220> FEATURE:
<221> NAME/KEY: MOD_RES
<222> LOCATION: 4
<223> OTHER INFORMATION: D-Alanine

<400> SEQUENCE: 12

Lys Val Thr Ala Met Lys Cys Phe Leu Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of the Sequence: Peptide 15
<220> FEATURE:
<221> NAME/KEY: MOD_RES
<222> LOCATION: 4
<223> OTHER INFORMATION: D-Alanine
<220> FEATURE:
<221> NAME/KEY: MOD_RES
<222> LOCATION: 7
<223> OTHER INFORMATION: D-Cysteine

<400> SEQUENCE: 13

Lys Val Thr Ala Met Lys Cys Phe Leu Leu
1               5                   10
```